US 12,402,785 B2

(12) United States Patent
Tanahashi et al.

(10) Patent No.: US 12,402,785 B2
(45) Date of Patent: Sep. 2, 2025

(54) ENDOSCOPE CAMERA HEAD (71) Applicant: Sony Olympus Medical Solutions Inc., Tokyo (JP)

(72) Inventors: Fuminori Tanahashi, Tokyo (JP); Kohtaro Amano, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 22 days.

(21) Appl. No.: 18/338,386

(22) Filed: Jun. 21, 2023

(65) Prior Publication Data

US 2023/0329536 A1    Oct. 19, 2023

Related U.S. Application Data

(62) Division of application No. 16/633,587, filed as application No. PCT/JP2018/018989 on May 16, 2018, now Pat. No. 11,717,143.

(30) Foreign Application Priority Data

Jul. 31, 2017    (JP) ................................ 2017-148486

(51) Int. Cl.
*A61B 1/04*    (2006.01)
*A61B 1/00*    (2006.01)

(52) U.S. Cl.
CPC .......... *A61B 1/042* (2013.01); *A61B 1/00066* (2013.01); *A61B 1/00105* (2013.01);
(Continued)

(58) Field of Classification Search
CPC ............ A61B 1/00066; A61B 1/00105; A61B 1/00128; A61B 1/00195; A61B 1/042
(Continued)

(56) References Cited

U.S. PATENT DOCUMENTS 4,552,131 A    11/1985 Omagari
4,740,058 A    4/1988 Hori et al.
(Continued)

FOREIGN PATENT DOCUMENTS

CN    101056576 A    10/2007
CN    102933254 A    2/2013
(Continued)

OTHER PUBLICATIONS

Extended European Search Report issued May 20, 2020 in European Patent Application No. 18840734.0, 7 pages.
(Continued)

*Primary Examiner* — Aaron B Fairchild
(74) *Attorney, Agent, or Firm* — XSENSUS LLP (57) ABSTRACT

An endoscope camera head 6 includes a first and a second members 8, 9 that are relatively rotatable about a first axis Ax1. The first member 8 has a first rotation-sliding surface 84 that extends in an annular shape about the first axis Ax1 as its center. The second member 9 has a second rotation-sliding surface 93 that engages with the first rotation-sliding surface 84 in a state in which movement to a direction of the first axis Ax1 relative to the first member 8 is restricted, and that rotation-slides relative to the first rotation-sliding surface 84 about the first axis Ax1. The second rotation-sliding surface 93 abuts only on a part of the first rotation-sliding surface 84, to expose a part of the first rotation-sliding surface 84 outside.

10 Claims, 9 Drawing Sheets

(52) U.S. Cl.
CPC ...... *A61B 1/00126* (2013.01); *A61B 1/00128* (2013.01); *A61B 1/00148* (2022.02); *A61B 1/00195* (2013.01); *A61B 1/04* (2013.01); *A61B 1/044* (2022.02)

(58) Field of Classification Search
USPC ........................................................ 600/137
See application file for complete search history.

(56) References Cited

U.S. PATENT DOCUMENTS

| | | | |
|---|---|---|---|
| 4,919,112 A * | 4/1990 | Siegmund | ............ A61B 1/0052 600/146 |
| 5,101,807 A | 4/1992 | Kawashima | |
| 5,205,280 A | 4/1993 | Dennison, Jr. et al. | |
| 5,406,418 A | 4/1995 | Deary | |
| 5,611,769 A * | 3/1997 | Monroe | ............. A61B 1/00124 348/E5.025 |
| 5,827,175 A | 10/1998 | Tanaka | |
| 6,679,874 B2 | 1/2004 | Miser | |
| 2006/0229495 A1 | 10/2006 | Frith | |
| 2010/0305400 A1 | 12/2010 | Onoda et al. | |
| 2011/0018988 A1 | 1/2011 | Kazakevich et al. | |
| 2013/0072754 A1 | 3/2013 | Okamoto et al. | |
| 2016/0235277 A1 | 8/2016 | Kudo et al. | |

FOREIGN PATENT DOCUMENTS

| | | |
|---|---|---|
| CN | 204394456 U | 6/2015 |
| CN | 106974610 A | 7/2017 |
| JP | S59-30115 U | 2/1984 |
| JP | S60-004918 A | 1/1985 |
| JP | S60-004919 A | 1/1985 |
| JP | H03-055023 A | 3/1991 |
| JP | H07-184845 A | 7/1995 |
| JP | H11-337846 A | 12/1999 |
| JP | 2000-227559 A | 8/2000 |
| JP | 2004-254807 A | 9/2004 |
| JP | 2005-040162 A | 2/2005 |
| JP | 2012-009771 A | 1/2012 |
| JP | 2013-056003 A | 3/2013 |

OTHER PUBLICATIONS

International Search Report and Written Opinion mailed on Aug. 7, 2018 for PCT/JP2018/018989 filed on May 16, 2018, 9 pages.

* cited by examiner

ENDOSCOPE CAMERA HEAD

CROSS-REFERENCE TO RELATED APPLICATIONS

The present application is a divisional of U.S. application Ser. No. 16/633,587, filed Jan. 24, 2020, which is based on PCT filing PCT/JP2018/018989, filed May 16, 2018, and claims priority to Japanese Patent Application No. 2017-148486, filed Jul. 31, 2017, the entire contents of each are incorporated herein by reference.

TECHNICAL FIELD

The present invention relates to an endoscope camera head that is used in an endoscope device to observe an inside of a subject, such as a human body and a mechanical structure.

BACKGROUND ART

Endoscope devices to observe inside a subject, such as a human body and a mechanical structure in a medical field or an industrial field has conventionally been known (for example, refer to Patent Literature 1).

An endoscope device described in Patent Literature 1 includes an endoscope (optical telescope) that captures and emits a subject image inside the subject, and an endoscope camera head (TV camera) that holds the endoscope and that forms an image from the subject image emitted from the endoscope. Moreover, the endoscope is rotatably held about an optical axis set inside with respect to the endoscope camera head.

Specifically, the endoscope camera head includes a coupler and a camera-head main unit.

The coupler has a bottomed-cylindrical shape in which an eyepiece of the endoscope can be engaged. Furthermore, at a bottom portion of the coupler, a through hole in a circular shape when viewed from top, piercing therethrough to both sides is formed.

The camera-head main unit includes a casing, and an imaging unit that is housed in the casing, and that forms an image of the subject image emitted from the endoscope. On an external surface of the casing, a concave portion that extends in a ring shape about a first axis as a center is formed.

Furthermore, the coupler (endoscope) is configured such that a rim portion of the through hole in the coupler engages with the concave portion of the casing, and that an outer surface of the rim portion slides on an inner surface (hereinafter, referred to as coupler rotation-sliding surface) of the concave portion, thereby rotating with respect to the camera-head main unit about the first axis as the center.

CITATION LIST

Patent Literature

Patent Literature 1: JP-A-2000-227559

DISCLOSURE OF INVENTION

Technical Problem

However, in the endoscope camera head described in Patent Literature 1, the coupler rotation-sliding surface is concealed with the casing rotation-sliding surface, and is not exposed outside. Therefore, when cleaning the endoscope camera head, it is difficult to clean a portion between the coupler rotation-sliding surface and the casing rotation-sliding surface with a brush. Moreover, it is difficult to let cleaning solution enter between the coupler rotation-sliding surface and the casing rotation-sliding surface. Accordingly, there is a problem that much time is consumed for cleaning.

The present invention is achieved in view of the above problem, and it is an object of the present invention to provide an endoscope camera head that enables to reduce cleaning time.

Solution to Problem

To solve the above-described problem and achieve the object, an endoscope camera head according to the present invention includes a first member and a second member that are capable of rotating relative to each other about a first axis, wherein the first member has a first rotation-sliding surface that extends in an annular shape about the first axis as a center, the second member engages with the first rotation-sliding surface in a state in which movement to a direction of the first axis is restricted relative to the first member, and has a second-rotation sliding surface that rotation-slides relatively to the first rotation-sliding surface about the first axis, and the second rotation-sliding surface abuts only on a part of the first rotation-sliding surface, to expose a part of the first rotation-sliding surface outside.

Moreover, in the above-described endoscope camera head according to the present invention, in the first member, a concave portion that extends in an annular shape about the first axis as a center is provided, the first rotation-sliding surface includes an inner surface of the concave portion, in the second member, a convex portion that extends in an annular shape about the first axis as a center, and that engages with the concave portion is provided, the second rotation-sliding surface includes an outer surface of the convex portion, and at a distal end of the convex portion, a groove portion that extends in a spiral shape about the first axis as a center, and respective parts of both end portions of which in a direction of the first axis are respectively positioned outside the concave portion is formed.

Moreover, in the above-described endoscope camera head according to the present invention, in the first member, a concave portion that extends in an annular shape about the first axis as a center is provided, the first rotation-sliding surface includes an inner surface of the concave portion, in the second member, a projection portion, a distal end of which extends in an arc shape about the first axis as a center, and that engages with the concave portion is provided, and the second rotation-sliding surface includes an outer surface of the projection portion.

Moreover, in the above-described endoscope camera head according to the present invention, the projection portion is provided in plurality in a direction of circle about the first axis as a center.

Moreover, the above-described endoscope camera head according to the present invention includes: a coupler holding an endoscope that captures and outputs a subject image; and a camera-head main unit that includes a casing supporting the coupler rotatably about the first axis, and an imaging unit that is housed in the casing, and that images the subject image emitted from the endoscope, wherein the first member is the casing, and the second member is the coupler.

Moreover, the above-described endoscope camera head according to the present invention includes: a coupler holding an endoscope that captures and outputs a subject image;

and a camera-head main unit that includes a casing supporting the coupler rotatably about the first axis, and an imaging unit that is housed in the casing, and that images the subject image emitted from the endoscope, wherein the first member is the coupler, and the second member is the casing.

Advantageous Effects of Invention

In the endoscope camera head according to the present invention, the first and the second members constituted of a coupler and a casing, respectively have the first and the second rotation sliding surfaces. The second rotation-sliding surface abuts only on a part of the first rotation-sliding surface, to expose a part of the first rotation-sliding surface outside.

Therefore, it is possible to insert a cleaning brush or to let cleaning solution reach the second rotation-sliding surface through the part of the first rotation-sliding surface exposed outside. Furthermore, by rotating the first and the second members relatively to each other about the first axis in a state in which the cleaning brush is inserted or the cleaning solution has entered therein, the first and the second rotation-sliding surfaces can be easily and efficiently cleaned.

Therefore, according to the endoscope camera head according to the present invention, an effect of reducing cleaning time is produced.

BEST MODE FOR CARRYING OUT THE INVENTION

Hereinafter, modes (hereinafter, embodiments) to implement the present invention will be described with reference to the drawings. Note that embodiments described below are not intended to limit the present invention. Furthermore, like reference symbols are assigned to like parts in descriptions of the drawings.

First Embodiment

Figure 1:
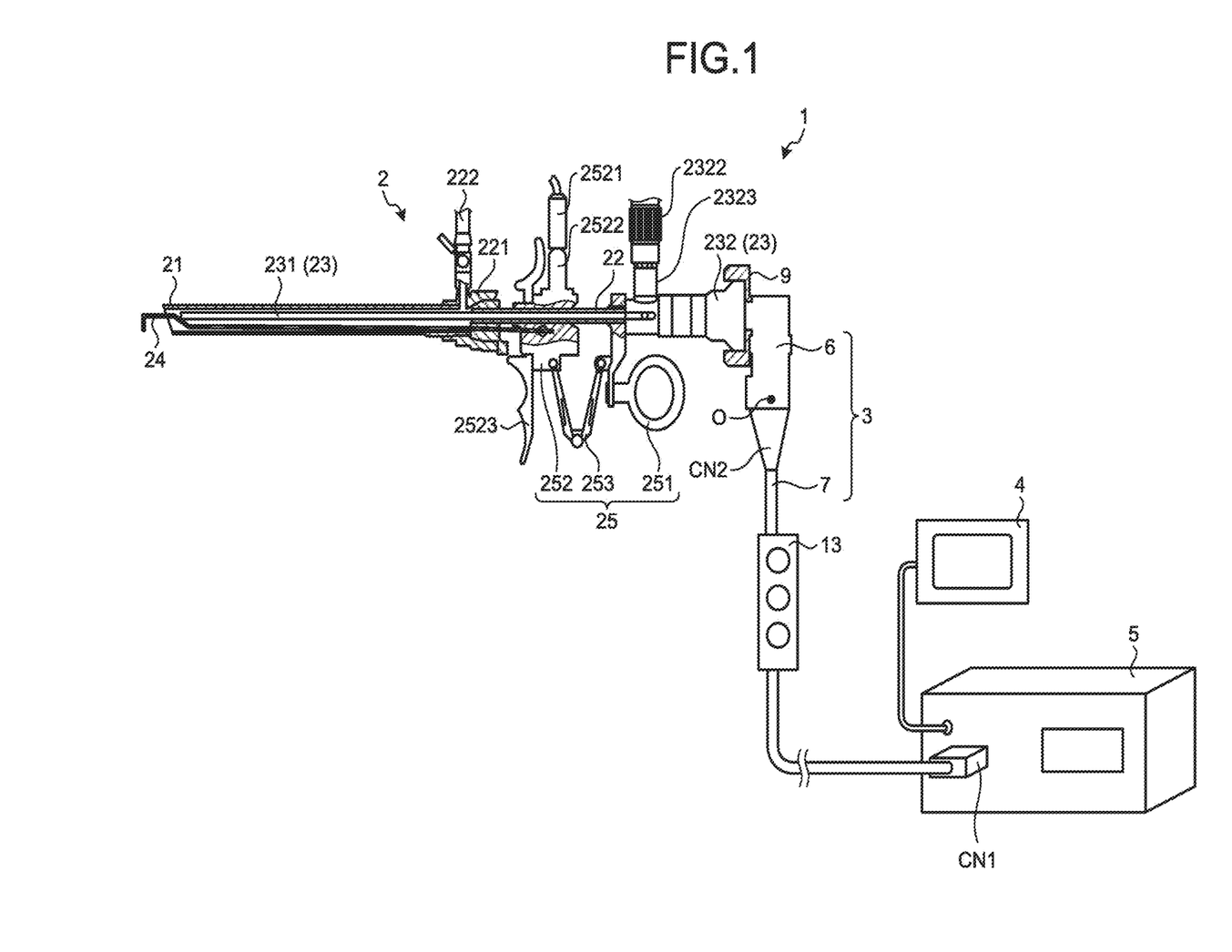
FIG. 1 is a diagram illustrating a schematic configuration of an endoscope device according to a first embodiment.

Schematic Configuration of Endoscope Device FIG. 1 is a diagram illustrating a configuration of an endoscope device 1 according to a first embodiment.

The endoscope device 1 is used in a medical field, and is a device to treat a living tissue (incision, and the like) while observing inside the living body. This endoscope device 1 includes, as illustrated in FIG. 1, a resectscope 2, an endoscope imaging device 3, a display device 4, and a control device 5.

The resectscope 2 is a part that is inserted into a living body, and that captures a subject image and treats a living tissue. This resectscope 2 includes, as illustrated in FIG. 1, a sheath 21, a guide tube 22, an endoscope 23, a resect electrode member 24, and a handle portion 25.

The sheath 21 is a part having a cylindrical shape, and inserted into a living body.

The guide tube 22 has a smaller outer diameter than an inner diameter of the sheath 21, and is inserted in the sheath 21. The guide tube 22 is fixed to the sheath 21 through a mounting member 221 (FIG. 1) on its distal end side (left side in FIG. 1).

In the mounting member 221, a water supply inlet 222 to infuse solution into the sheath 21, and to supply the solution from a distal end of the sheath 21 is provided.

The endoscope 23 is a part of capturing a subject image, and includes, as illustrated in FIG. 1, an insertion portion 231 and an eyepiece 232.

The insertion portion 231 is fixed inside the guide tube 22, and is inserted into the sheath 21. Inside this insertion portion 231, an optical system that is constituted of one or more lenses, and that gathers the subject image is provided.

The eyepiece 232 is connected to a proximal end (right end portion in FIG. 1) of the insertion portion 231. Inside this eyepiece 232, an eyepiece optical system 2321 (refer to FIG. 2) that emits the subject image gathered by the optical system inside the insertion portion 231 from the eyepiece 232 to outside is provided. The eyepiece 232 is formed in a tapered shape in which a diameter increases toward a right side, and to an increased-diameter portion, the endoscope imaging device 3 is detachably connected.

To the eyepiece 232, a light source connector 2323 to connect a light guide 2322 is arranged. That is, light supplied to the light guide 2322 from a light source device (not shown) is supplied to the insertion portion 231 through the eyepiece 232. The light supplied to the insertion portion 231 is emitted from the distal end of the insertion portion 231, and is irradiated inside a living body. The light irradiated inside the living body and reflected in the living body (subject image) is emitted from the eyepiece 232 through the optical system inside the insertion portion 231 and the eyepiece optical system 2321.

The resect electrode member 24 is inserted in the sheath 21 through the mounting member 221, and its distal end protrudes out from the distal end of the sheath 21. The resect electrode member 24 brought in contact with a living tissue at its end portion, and treats the living tissue with a high frequency current.

The handle portion 25 is a part with which a doctor or the like holds the resectscope 2, and operates the resect electrode member 24. This handle portion 25 includes, as illustrated in FIG. 1, a fixing ring 251, a slider 252, and a spring member 253.

The fixing ring 251 is a part on which a doctor or the like hooks his/her thumb, and is fixed to the guide tube 22.

The slider 252 has the guide tube 22 inserted therethrough, to be configured to be movable in a left and right direction in FIG. 1 along the guide tube 22.

To this slider 252, the resect electrode member 24 is fixed as illustrated in FIG. 1. That is, the resect electrode member 24 reciprocates in a left and right direction in FIG. 1 inside the sheath 21, along with movement of the slider 252.

Moreover, in the slider 252, a power source connector 2522 to connect a high-frequency power cord 2521 connected to a high frequency power source (not shown) is provided. This power source connector 2522 is electrically connected with the resect electrode member 24 through a lead (not shown).

Furthermore, in the slider 252, a finger hook member 2523 on which fingers other than a thumb of a doctor or the like are hooked, to move the slider 252 (to reciprocate the resect electrode member 24) is arranged.

The spring member 253 has a substantially U-shape, and one end there of is attached to the fixing ring 251, and the other end is attached to the slider 252. The spring member 253 applies pressure in such a direction that the slider 252 is apart from the fixing ring 251.

That is, a doctor or the like hooks his/her fingers on the fixing ring 251 and the finger hook member 2523, and pulls the finger hook member 2523, resisting the pressure of the spring member 253, to thereby move the slider 252 in rightward in FIG. 1 (to move the resect electrode member 24 rightward in FIG. 1). On the other hand, when the doctor or the like moves the fingers off the finger hook member 2523, the slider 252 (the resect electrode member 24) moves leftward in FIG. 1 by the pressure of the spring member 253.

The endoscope imaging device 3 is detachably connected to the eyepiece 232 of the resectscope 2 (the endoscope 23). The endoscope imaging device 3 images a subject image (a subject image emitted from the eyepiece 232) captured by the endoscope 23, and outputs an image signal (RAW signal) from this imaging under control of the control device 5. The image signal is, for example, an image signal of 4K or higher.

A detailed configuration of the endoscope imaging device 3 will be described later.

The display device 4 is constituted of a display using a liquid crystal, an organic EL (electroluminescence), or the like, and displays, under a control of the control unit 5, an observation image based on a video signal from the control unit 5.

The control device 5 includes a (CPU) central processing unit, and controls operations of the endoscope imaging device 3, the display device 4, and the light source device (not shown) in a centralized manner. For example, the control device 5 generates a video signal for display by subjecting the image signal (RAW signal) output from the endoscope imaging device 3 to predetermined image processing. The control device 5 then causes the display device 4 to display an observation image based on the video signal.

Configuration of Endoscope Imaging Device

Next, a configuration of the endoscope imaging device will be described.

Figure 2:
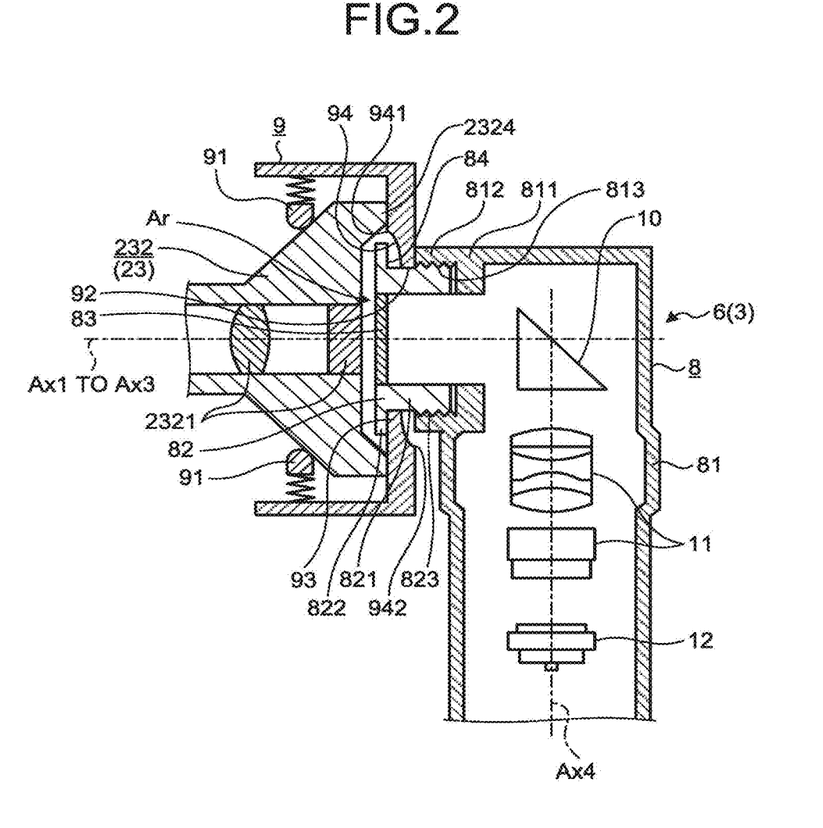
FIG. 2 is a cross-section illustrating a connecting portion between an eyepiece and an endoscope camera head.
Figure 3:
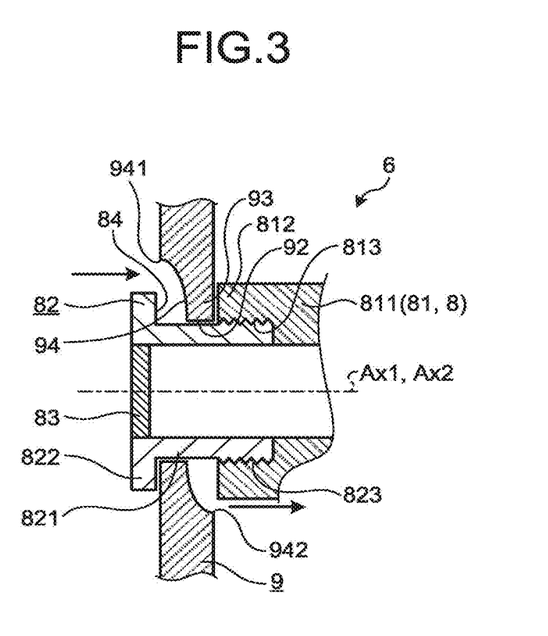
FIG. 3 is an enlarged view of a part of FIG. 2.

FIG. 2 is a cross-section illustrating a connecting portion between the eyepiece 232 and an endoscope camera head 6. FIG. 3 is an enlarged view of a part of FIG. 2. The endoscope imaging device 3 includes, as illustrated in FIG. 1 or FIG. 2, the endoscope camera head 6 and a cable 7 (FIG. 1).

The endoscope camera head 6 is a part detachably connected to the eyepiece 232 as illustrated in FIG. 1 or FIG. 2. This endoscope camera head 6 includes, as illustrated in FIG. 2, a casing 8, a coupler 9, a prism 10, a lens unit 11, and an imaging unit 12.

The casing 8 corresponds to a first member according to the present invention. This casing 8 includes, as illustrated in FIG. 2 or FIG. 3, a casing main body 81 and an attachment bush 82.

The casing main body 81 is a case that houses the respective parts 10 to 12. In this casing main body 81, a protrusion portion 811 in a cylindrical shape, communicating inside and outside of the casing main body 81 is arranged, as illustrated in FIG. 2 or FIG. 3.

In the protrusion portion 811, as illustrated in FIG. 2 or FIG. 3, a jut-out portion 812 that juts out toward a left side in FIG. 2 and FIG. 3 is arranged on an outer circumferential side. This jut-out portion 812 has an outer diameter substantially the same as the protrusion portion 811, is formed in a cylindrical shape having an inner diameter larger than the protrusion portion 811, and is integrated with a distal end of the protrusion portion 811, coaxially with the protrusion portion 811. Moreover, on an inner circumferential surface of the jut-out portion 812, a screw groove 813 is formed.

The attachment bush 82 is a part to attach the coupler 9 to the casing 8. This attachment bush 82 includes, as illustrated in FIG. 2 or FIG. 3, a bush main body 821 and a jut-out portion 822.

The bush main body 821 has an inner diameter substantially the same as the protrusion portion 811, and is formed in a cylindrical shape having an outer diameter substantially the same as the inner diameter of the jut-out portion 812. Furthermore, on an outer circumferential surface of the bush main body 821, a screw groove 823 is formed as illustrated in FIG. 2 or FIG. 3.

The jut-out portion 822 extends out from a rim portion at a left end in FIG. 2, FIG. 3 on the outer circumferential surface of the bush main body 821, and is formed in an annular shape having an outer diameter substantially the same as the jut-out portion 812.

The casing main body 81 and the attachment bush 82 are fixed to each other, by engaging the screw grooves 813 and 823 with each other. In this state, center axes of the casing main body 81 and the attachment bush 82 agree with each other. The center axis corresponds to a first axis Ax1 (FIG. 2, FIG. 3) according to the present invention. Moreover, in the attachment bush 82, an optical device 83 of sapphire glass, or the like is fixed as illustrated in FIG. 2 or FIG. 3.

In the state in which the casing main body 81 and the attachment bush 82 are fixed to each other, with surfaces of respective ends of the jut-out portion 812 and 822 facing each other, and the outer circumferential surface of the bush main body 821, a concave portion 84 (FIG. 2, FIG. 3) extending in an annular shape having the first axis Ax1 in center is provided. An inner surface of the concave portion 84 (the surfaces of respective ends of the jut-out portions 812 and 822 facing each other, and the outer circumferential surface of the bush main body 821) corresponds to a first rotation-sliding surface according to the present invention.

The coupler 9 is a part corresponding to a second member according to the present invention. This coupler 9 has a bottomed-cylindrical shape in which the eyepiece 232 can be fitted therein as illustrated in FIG. 2.

On an inner circumferential surface of this coupler 9, a pressurizing portion 91 is arranged as illustrate in FIG. 2.

This pressurizing portion 91 has elasticity enable to move in a direction of separation in adjoining isolation relative to a center axis Ax2 of the coupler 9, and applies pressure to the eyepiece 232 toward a bottom portion of the coupler 9, by abutting on an outer circumferential surface of the eyepiece 232 that is fitted in the coupler 9. In the first embodiment, four pieces of the pressurizing portions 91 are provided, and are arranged to be rotationally symmetric at 90° about the center axis Ax2. Note that in the state in which the eyepiece 232 is fitted inside the coupler 9, an optical axis Ax3 of the endoscope 23 (FIG. 2, hereinafter, referred to as endoscope optical axis Ax3) agree with the center axis Ax2. Moreover, on an outer circumferential surface of the eyepiece 232 on a right end portion in FIG. 2, an expanding portion 2324 that expands toward a right side in FIG. 2 is provided on the entire circumference. Therefore, when the eyepiece 232 is pressurized toward the bottom portion of the coupler 9 by the pressurizing portion 91, the expanding portion 2324 abuts on the bottom portion. Thus, space Ar (FIG. 2) is formed between the optical device 83 and the eyepiece optical system 2321.

Moreover, the bottom portion of the coupler 9 is constituted of a plate in a circular shape when viewed from top, each plane of which is perpendicular to the center axis Ax2. Moreover, the bottom portion has a thickness substantially the same as a width of the concave portion 84. Furthermore, in the bottom portion, a through hole 92 that penetrates through to its front and rear surfaces, and that has a circular shape when viewed from top having an inner diameter substantially the same as an outer diameter of the bush main body 821 is formed. The coupler 9 is attached to the casing 8 as a rim portion of the through hole 92 engages with (fits in) the concave portion 84 in a state in which an opening of the bottomed-cylindrical shape is directed to the left side in FIG. 2. In this state, the center axis Ax2 agrees with the first axis Ax1. Moreover, the coupler 9 is restricted its movement to a direction of the first axis Ax1 relative to the casing 8, and is rotatable relative to the casing 8 about the first axis Ax1 (the center axis Ax2).

Therefore, the endoscope camera head 6 is structured rotatable about the first axis Ax1 (the center axis Ax2, the endoscope optical axis Ax3), relative to the eyepiece 232 of the endoscope 23 through the coupler 9. Moreover, the endoscope camera head 6 is structured such that its center of gravity O (FIG. 1) is positioned off the first axis Ax1 (a rotation center axis relative to the eyepiece 232). The endoscope camera head 6 rotates about the first axis Ax1 irrespective of rotation about the first axis Ax1 of the resectscope 2, and is structured to maintain an orientation in which an optical axis Ax4 (FIG. 2, hereinafter, referred to as in-case optical axis Ax4) set inside the casing 81 is along a vertical direction (orientation in which the center of gravity O is positioned below the first axis Ax1) all the time.

The rim portion of the through hole 92 extends in an annular shape about the first axis Ax1, and corresponds to a convex portion 93 (FIG. 2, FIG. 3) according to the present invention. Furthermore, the outer surface of the convex portion 93 is a portion that slides on the inner surface of the concave portion 84, and corresponds to a second rotation-sliding surface according to the present invention.

At a distal end of the convex portion 93 (inner surface of the through hole 92), a groove portion 94 is formed as illustrated in FIG. 2 or FIG. 3.

Figure 4:
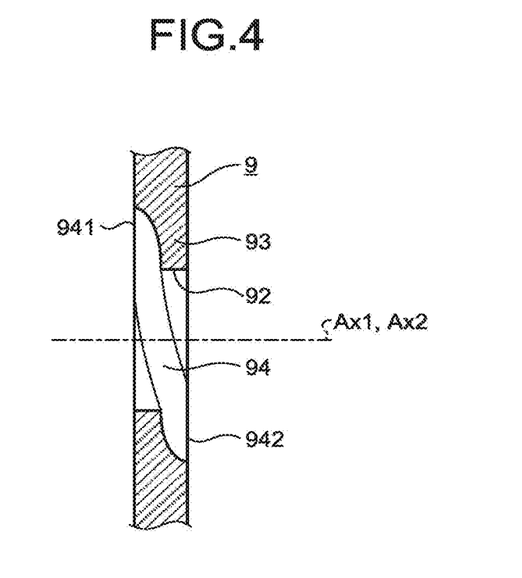
FIG. 4 is a diagram illustrating a groove portion.

FIG. 4 is a diagram illustrating the groove portion 94. The groove portion 94 extends in a spiral shape about the first axis Ax1 (the center axis Ax2) at the distal end of the convex portion 93 as illustrated in FIG. 4. In the state in which the coupler 9 is attached to the casing 8, a part of both end portions 941, 942 in the direction of the first axis Ax1 in the groove portion 94 is respectively positioned outside the concave portion 84.

That is, in the state in which relative rotation of the casing 8 and the coupler 9 about the first axis Ax1 is stopped, the outer surface of the convex portion 93 (the second rotation-sliding surface according to the second embodiment) abuts only on a part of the inner surface (the first rotation-sliding surface according to the present invention) of the concave portion 84 by having the groove portion 94, enabling to expose a part of the inner surface of the concave portion 84 outside.

The prism 10 is arranged on the first axis Ax1 and on the in-case optical axis Ax4 as illustrated in FIG. 2, and polarizes a subject image captured by the endoscope 23 to change the traveling direction. Specifically, the prism 10 polarizes a subject image (subject image that travels along the endoscope optical axis Ax3) that is emitted from the eyepiece 232 and taken into the casing 8 through the optical device 83, to change the traveling direction by 90° to travel along the in-case optical axis Ax4.

The lens unit 11 is arranged on the in-case optical axis Ax4 as illustrated in FIG. 2. This lens unit 11 is constituted of one or plural lenses, and forms an image of the subject image entering through the prism 10 on an imaging surface of the imaging unit 12. Moreover, the lens unit 11 is provided with an optical zoom function (not shown) that changes an angle of view by moving the one or plural lenses under control of the control device 5 or an operating unit 13 (FIG. 1), and a focus mechanism (not shown) that changes a focal point.

The imaging unit 12 is arranged on the in-case optical axis Ax4 as illustrated in FIG. 2. The imaging unit 12 images a subject image formed by the lens unit 11 under control of the control device 5. This imaging unit 12 is constituted of a sensor chip in which an imaging device (not shown) that receives a subject image formed by the lens unit 11 to convert into an electrical signal, such as a CCD (charge coupled device) and a CMOS (complementary metal oxide semiconductor), and a signal processing unit (not shown) that outputs an image signal by subjecting the electrical signal (analog signal) from the imaging device to a signal processing (A/D conversion, and the like), and the like are integrally formed, and outputs the image signal (RAW signal (digital signal)) subjected to the A/D conversion. Note that the signal processing unit described above may be prepared as a separate unit without integrating with the imaging device.

The cable 7 is detachably connected at its one end to the control device 5 through a connector CN1 (FIG. 1), and is detachably connected at the other end to the endoscope camera head 6 through a connector CN2 (FIG. 1). The cable 7 transmits an image signal output from the endoscope camera head 6 to the control device 5, and transmits a control signal, a synchronization signal, a clock, power, and the like output from the control device 5 to the endoscope camera head 6.

Note that in transmission of an image signal from the endoscope camera head 6 through the cable 7, the image signal may be transmitted in an optical signal, or may be transmitted in an electrical signal. The same applies to transmission of the control signal, the synchronization signal, and the clock from the control device 5 to the endoscope camera head 6 through the cable 7.

Moreover, in the cable 7, the operating unit 13 that receives various kinds of operations from a doctor and the like (for example, an instruction of image quality adjustment (white balance adjustment, brightness adjustment, and the like) of an observation image, an instruction to change an angle of view or a focal point of the lens unit 11, and the like) is provided as illustrated in FIG. 1.

According to the first embodiment described above, following effects are produced.

The endoscope camera head 6 according to the first embodiment includes the casing 8 having the concave portion 84 that extends in an annular shape about the first axis Ax1, and the coupler 9 having the convex portion 93 that extends in an annular shape about the first axis Ax1 and that engages with the concave portion 84. Moreover, at the distal end of the convex portion 93, the groove portion 94 is formed that extends in a spiral shape about the first axis Ax1, and in which respective parts of the both end portions 941 and 942 in the direction of the first axis Ax1 are positioned outside the concave portion 84, respectively. The outer surface of the convex portion 93 abuts only on a part of the inner surface of the concave portion 84 by having the groove portion 94, in the state in which relative rotation of casing 8 and the coupler about the first axis Ax1 is stopped, to expose a part of the inner surface of the concave portion 84.

Therefore, by relatively rotating the casing 8 and the coupler 9 about the first axis Ax1 in a state in which the endoscope camera head 6 is immersed in cleaning solution, the cleaning solution flows into the groove portion 94 from the end portion 941 as indicated by an arrow in FIG. 3, and follows the groove portion 94 to flows out of the groove portion 94 from the end portion 942. That is, it is possible to clean a portion between the inner surface of the concave portion 84 and the outer surface of the convex portion 93 easily and effectively. Note that depending on a rotation direction of the casing 8 and the coupler 9, a flowing direction of the cleaning solution indicated by the arrow in FIG. 3 is to be opposite.

Therefore, according to the endoscope camera head 6 according to the first embodiment, an effect of reducing the cleaning time is produced.

Modification 1-1 of First Embodiment

Figure 5:
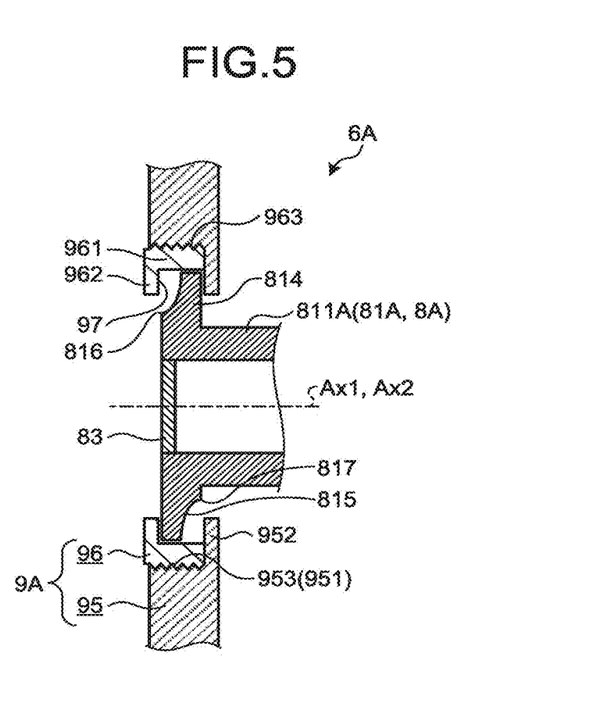
FIG. 5 is a diagram illustrating a modification 1-1 of the first embodiment.
Figure 6:
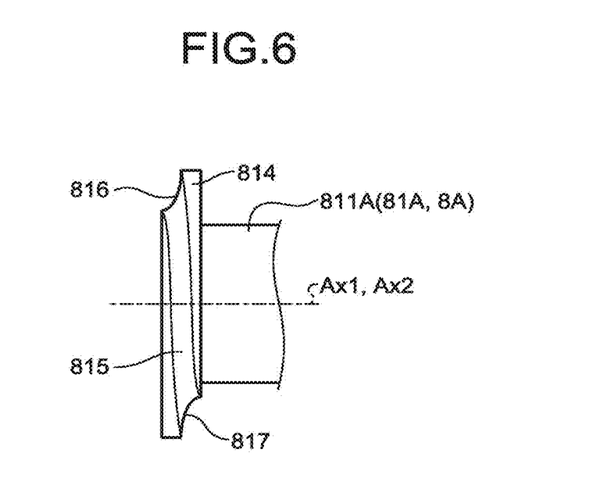
FIG. 6 is a diagram illustrating the modification 1-1 of the first embodiment.

FIG. 5 and FIG. 6 are diagrams illustrating a modification 1-1 of the first embodiment. Specifically, FIG. 5 is a diagram corresponding to FIG. 3. FIG. 6 is a diagram illustrating a groove portion 815 according to the modification 1-1.

In the endoscope camera head 6 according to the first embodiment described above, the first member according to the present invention is the casing 8, and the second member according to the present invention is the coupler 9, but it is not limited thereto. For example, as an endoscope camera head 6A according to the modification 1-1 illustrated in FIG. 5 and FIG. 6, the first member according to the present invention may be a coupler 9A, and the second member according to the present invention may be a casing 8A.

Specifically, the coupler 9A according to the modification 1-1 includes a coupler main body 95 and an attachment bush 96 as illustrated in FIG. 5.

The coupler main body 95 has a bottomed-cylindrical shape enabling to be engaged in the eyepiece 232, similarly to the coupler 9 described in the first embodiment.

In a bottom portion of this coupler main body 95, a through hole 951 that penetrates through to its front and rear surfaces, and that has a circular shape when viewed from top is formed as illustrated in FIG. 5. Moreover, on an inner circumferential surface of the through hole 951, a jut-out portion 952 that extends toward the center axis Ax2 and that has an annular shape around the center axis Ax2 as its center is formed on a right end rim side in FIG. 5. Furthermore, on the inner circumferential surface of the through hole 951, a screw groove 953 is formed on a left side in FIG. 5 relative to the jut-out portion 952.

The attachment bush 96 is a member to attach the coupler 9A to the casing 8A. This attachment bush 96 includes a bush main body 961 and a jut-out portion 962 as illustrated in FIG. 5.

The bush main body 961 has an outer diameter substantially the same as an inner diameter of the through hole 951, and is formed in a cylindrical shape having an inner diameter larger than the inner diameter of the jut-out portion 952. Moreover, on an outer circumferential surface of the bush main body 961, a screw groove 963 is formed as illustrated in FIG. 5.

The jut-out portion 962 protrudes toward the center axis Ax2 from a left end rim side of an inner circumferential surface of the bush main body 961 in FIG. 1, and is formed in an annular shape having an inner diameter substantially the same as the jut-out portion 952.

The coupler main body 95 and the attachment bush 96 are fixed to each other, by engaging the screw grooves 953 and 963 with each other. In this state, a center axis of the attachment bush 96 agrees with the center axis Ax2 of the coupler main body 95.

In the state in which the coupler main body 95 and the attachment bush 96 are fixed to each other, with surfaces of respective ends of the jut-out portions 952 and 962 facing each other, and the inner circumferential surface of the bush main body 961, a concave portion 97 extending in an annular shape having the first axis Ax1 in center is provided as illustrated in FIG. 5. An inner surface of the concave portion 97 (the surfaces of respective ends of the jut-out portions 952 and 962 facing each other, and the inner circumferential surface of the bush main body 961) corresponds to the first rotation-sliding surface according to the present invention.

Moreover, the casing 8A according to the modification 1-1 is structured without the attachment bush 82, omitting from the casing 8 described in the first embodiment above, and is constituted of only of the casing 81A having a protrusion portion 811A in a different shape from the protrusion portion 811.

The protrusion portion 811A has a bottomed-cylindrical shape that communicates inside and outside of the casing main body 81A, similarly to the protrusion portion 811 described in the first embodiment. Moreover, in the protrusion portion 811A, the optical device 83 is fixed as illustrated in FIG. 5. Furthermore, in the protrusion portion 811A, a convex portion 814 that protrudes out from the left end rim on the outer circumferential surface in FIG. 5, and that has an annular shape having the first axis Ax1 as its center is provided. This convex portion 814 has thickness substantially the same as a width of the concave portion 97. Moreover, the convex portion 814 has an outer diameter substantially the same as the inner diameter of the bush main body 961. The coupler 9A is attached to the casing 8A as the convex portion 814 engages with (fits in) the concave portion 97. In this state, the center axis Ax2 agrees with the first axis Ax1. Moreover, the coupler 9A is restricted its movement to a direction of the first axis Ax1 relative to the casing 8A, and is rotatable relative to the casing 8A about the first axis Ax1 (the center axis Ax2).

The outer surface of the convex portion 814 is a portion that slides on the inner surface of the concave portion 97, and corresponds to the second rotation-sliding surface according to the present invention.

At a distal end of the convex portion 814, a groove portion 815 is formed as illustrated in FIG. 5 or FIG. 6.

The groove portion 815 extends in a spiral shape about the first axis Ax1 at the distal end of the convex portion 814 as illustrated in FIG. 6. In the state in which the coupler 9A is attached to the casing 8A, respective parts of the both end portions 816 and 817 in the direction of the first axis Ax1 in the groove portion 815 are positioned outside the concave portion 97, respectively.

That is, the outer surface of the convex portion 814 (the second rotation-sliding surface according to the present invention) abuts only on a part of the inner surface of the concave portion 97 (the first rotation-sliding surface according to the present invention) by having the groove portion 815, in the state in which relative rotation of casing 8 and the coupler 9A about the first axis Ax1 is stopped, to expose a part of the inner surface of the concave portion 97.

As the modification 1-1 described above, also when the first member according to the present invention is the coupler 9A, and the second member according to the present invention is the casing 8A, effects similar to those of the first embodiment described above are produced.

Second Embodiment

Next, a second embodiment of the present invention will be described.

Figure 7:
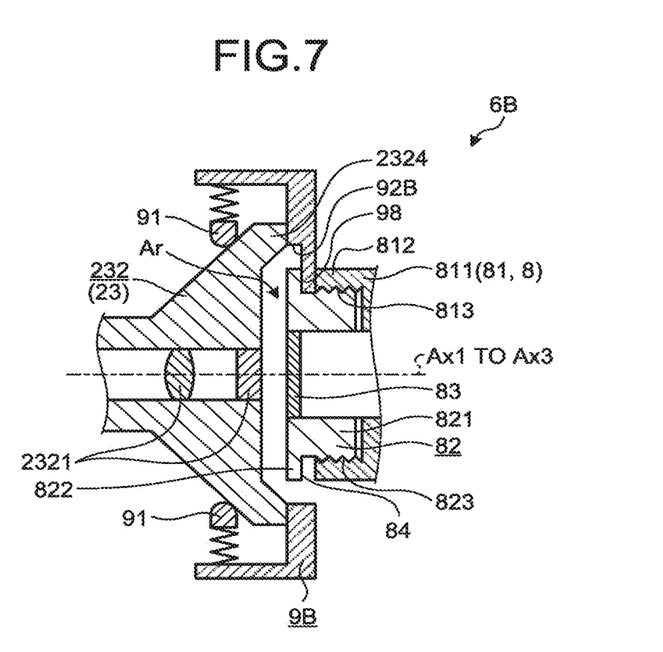
FIG. 7 is a cross-section illustrating a connecting portion between an eyepiece and an endoscope camera head according to a second embodiment.
Figure 8:
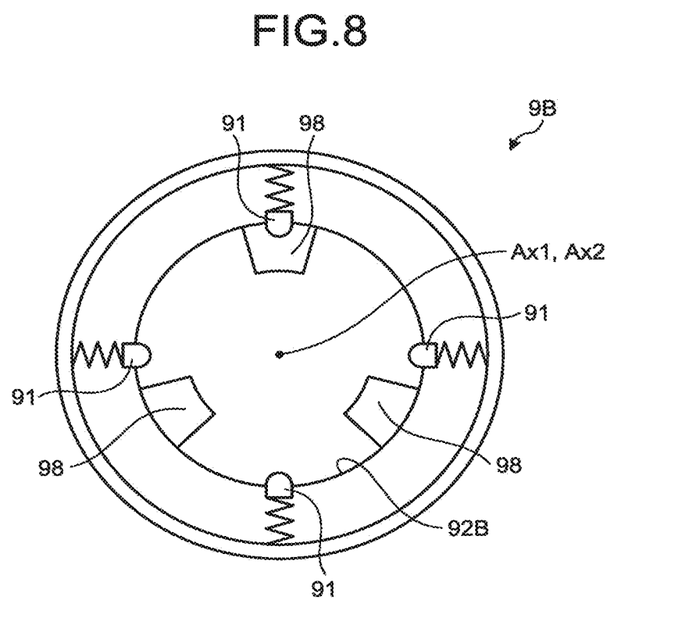
FIG. 8 is a diagram illustrating a coupler according to a second embodiment.

Hereinafter, same reference symbols are assigned to same components as the first embodiment described above, and detailed description thereof is omitted or simplified. FIG. 7 is a cross-section illustrating a connecting portion between the eyepiece 232 and an endoscope camera head 6B according to the second embodiment. FIG. 8 is a diagram illustrating a coupler 9B according to the second embodiment. Specifically, FIG. 8 is a diagram of a view of the coupler 9B from a side on which the eyepiece 232 is fitted in.

In the endoscope camera head 6B according to the second embodiment, as illustrated in FIG. 7 or FIG. 8, the coupler 9B in a different shape from the coupler 9 is used for the endoscope camera head 6 described in the first embodiment above.

The coupler 9B has a through hole 92B having an inner diameter larger than the inner diameter of the through hole 92 when compared with the coupler 9 described in the first embodiment. The inner diameter of this through hole 92B is set to be larger than the outer diameter of the jut-out portions 812, 822. Moreover, on an inner circumferential surface of the through hole 92B, a projection portion 98 that projects toward the center axis Ax2 from a right end rim side in FIG. 7, and in which a proximal end thereof extends in an arc shape having the center axis Ax2 (the first axis Ax1) as its center is formed. This projection portion 98 has thickness substantially the same as the width of the concave portion 84. In the second embodiment, three pieces of the projection portions 98 are provided, and are arranged to be rotationally symmetric at 120° about the center axis Ax2 (the first axis Ax1). Furthermore, a locus of distal ends of the three projection portion 98 forms a circular shape having a diameter substantially the same as the outer diameter of the bush main body 821. The coupler 9B is attached to the casing 8 as the three projection portions 98 respectively engage with (fit in) the concave portion 84 in a state in which an opening of the bottomed-cylindrical shape is directed to the left side in FIG. 7. In this state, the center axis Ax2 agrees with the first axis Ax1. Moreover, the coupler 9B is restricted its movement to a direction of the first axis Ax1 relative to the casing 8, and is rotatable relative to the casing 8 about the first axis Ax1 (the center axis Ax2).

The outer surface of the projection portion 98 is a portion that slides on the inner surface of the concave portion 84, and corresponds to the second rotation-sliding surface according to the present invention.

That is, the outer surface of the projection portion 98 (the second rotation-sliding surface according to the present invention) abuts only on a part of the inner surface (the first rotation-sliding surface according to the present invention) of the concave portion 84 in a state in which relative rotation of the casing 8 and the coupler 9B about the first axis Ax1 is stopped, to expose a part of the inner surface of the concave portion 84.

According to the second embodiment described above, following effects are produced.

Figure 9:
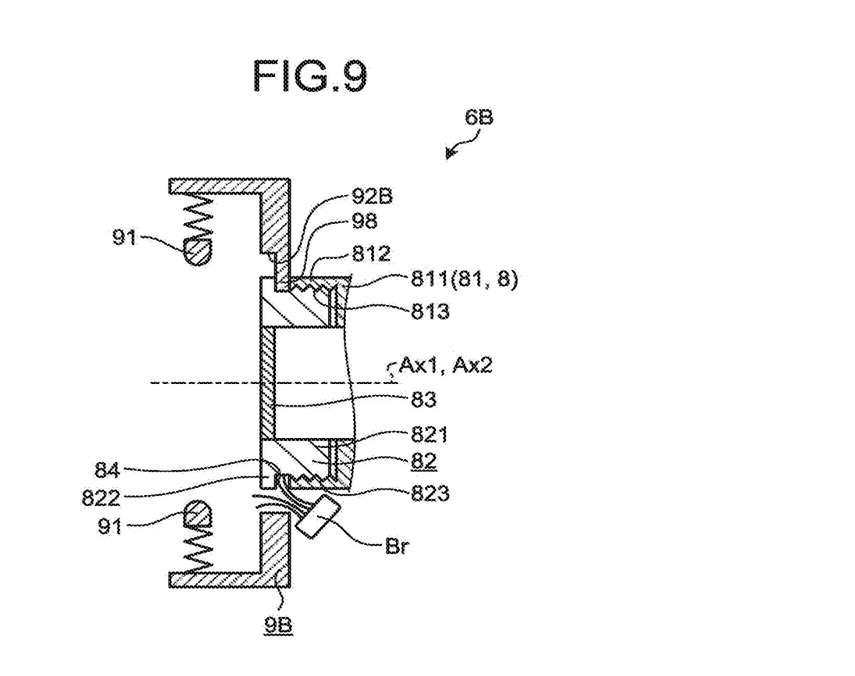
FIG. 9 is a diagram illustrating an effect of the second embodiment.
Figure 10:
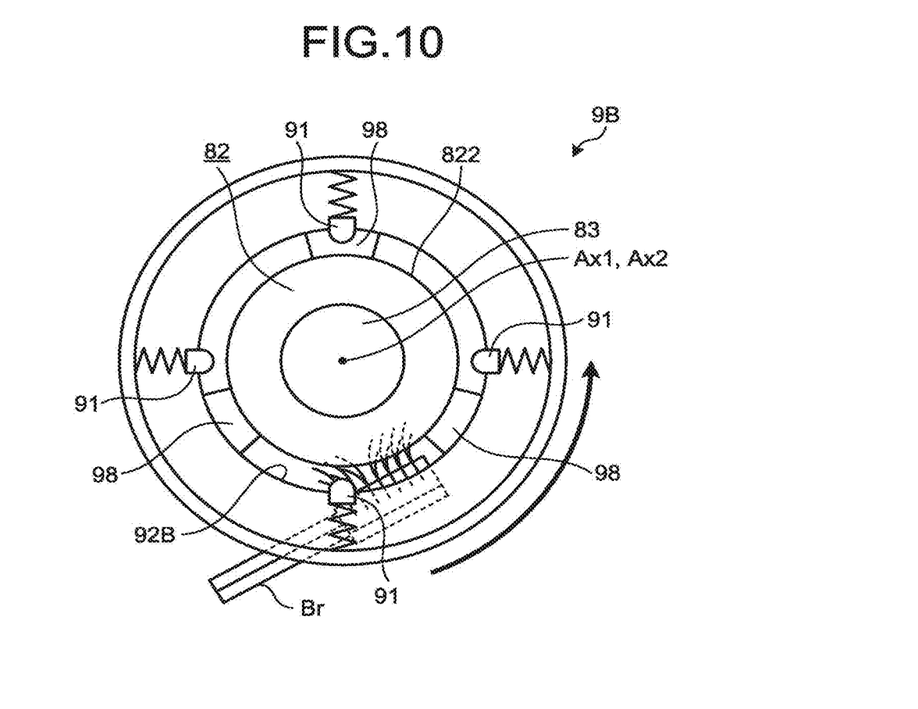
FIG. 10 is a diagram illustrating an effect of the second embodiment.

FIG. 9 and FIG. 10 are diagrams illustrating an effect of the second embodiment. Specifically, FIG. 9 is a diagram corresponding to FIG. 7. FIG. 10 is a diagram corresponding to FIG. 8.

The endoscope camera head 6B according to the second embodiment includes the casing 8 having the concave portion 84 that extends in an annular shape having the first axis Ax1 as its center, and the coupler 9B having the projection portion 98, the distal end of which extends in an arc shape having the first axis Ax1 as its center and engages with the concave portion 84. The outer surface of the projection portion 98 abuts only on a part of the inner surface of the concave portion 84 in a state in which relative rotation of the casing 8 and the coupler 9B about the first axis Ax1 is stopped, to expose a part of the inner surface of the concave portion 84 outside.

Therefore, the inner surface of the concave portion 84 can be cleaned as described below.

That is, as illustrated in FIG. 9 or FIG. 10, in a gap between a rim portion of the through hole 92B and the jut-out portion 812, a cleaning brush Br is brought into contact with the inner surface of the concave portion 84 from a portion at which the projection portion 98 is not formed. By rotating the coupler 9B and the cleaning brush Br about the first axis Ax1 with respect to the casing 8 as indicated by an arrow in FIG. 10, a portion between the inner surface of the concave portion 84 and the outer surface of the projection portion 98 can be cleaned easily and efficiently.

Therefore, according to the endoscope camera head 6B according to the second embodiment, an effect of reducing cleaning time is produced.

Moreover, in the gap between the rim portion of the through hole 92B and the jut-out portion 812, a portion at which the projection portion 98 is not formed is to be a ventilation hole that communicates inside and outside a space Ar. For this, it is possible to suppress formation of condensation on the eyepiece optical system 2321 or the optical device 83, and to reduce drying time when condensation is formed.

Particularly, three pieces of the projection portions 98 are provided at positions to be rotationally symmetric at 120° about the first axis Ax1. For this, the ventilation holes that communicate inside and outside the space Ar can be spaced uniformly, and it is possible to suppress formation of condensation on the eyepiece optical system 2321 and the optical device 83 effectively, and to significantly reduce drying time when condensation is formed.

Modification 2-1 of Second Embodiment

Figure 11:
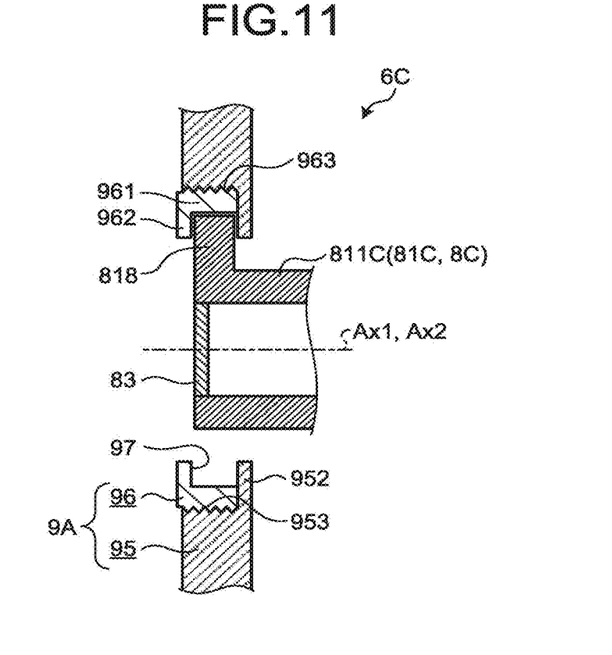
FIG. 11 is a diagram illustrating a modification 2-1 of the second embodiment.
Figure 12:
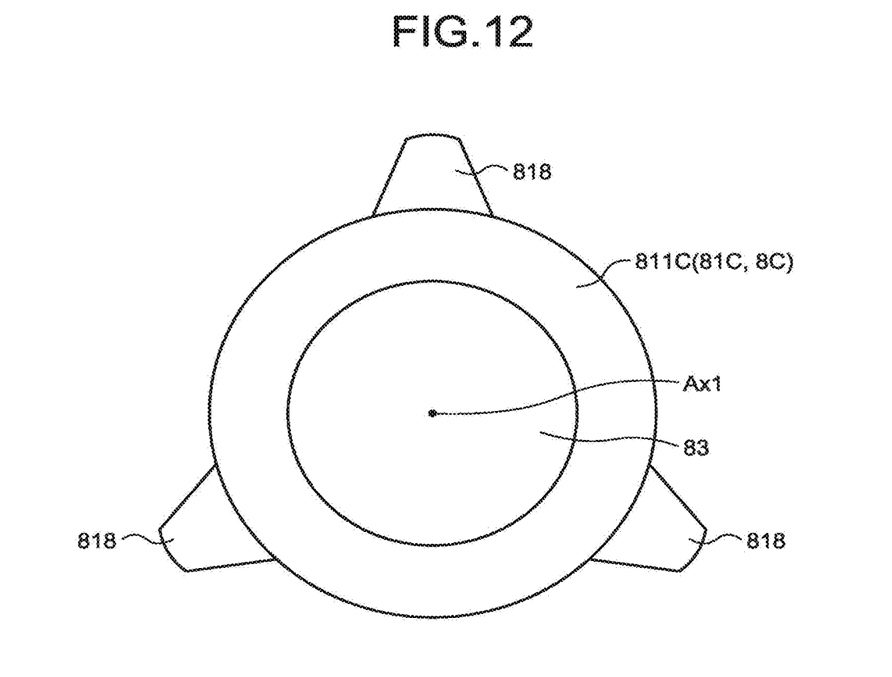
FIG. 12 is a diagram illustrating the modification 2-1 of the second embodiment.

FIG. 11 and FIG. 12 are diagrams illustrating a modification 2-1 of the second embodiment. Specifically, FIG. 11 is a cross section illustrating a connecting portion between a casing 8C and the coupler 9A according to the modification 2-1. FIG. 12 is a view of the casing 8C from a distal end side of a protrusion portion 811C.

In the endoscope camera head 6B according to the second embodiment described above, the first member according to the present invention is the casing 8, and the second member according to the present invention is the coupler 9B, but it is not limited thereto. For example, as an endoscope camera head 6C according to the modification 2-1 illustrated in FIG. 11 and FIG. 12, the first member according to the present invention may be the coupler 9A, and the second member according to the present invention is the casing 8C.

Specifically, the coupler 9A according to the modification 2-1 has the same configuration as the coupler 9A described in the modification 1-1.

Moreover, the casing 8C according to the modification 2-1 is structured without the attachment bush 82, omitting from the casing 8 described in the second embodiment, and is constituted of only of a casing main body 81C having the protrusion portion 811C in a different shape from the protrusion portion 811 as illustrated in FIG. 11 or FIG. 12.

The protrusion portion 811C has a cylindrical shape that communicates inside and outside the casing main body 81C, similarly to the protrusion portion 811 described in the second embodiment. Moreover, inside the protrusion portion 811C, the optical device 83 is fixed as illustrated in FIG. 11. Furthermore, in the protrusion portion 811C, a projection portion 818 that protrudes from a left end rim side in FIG. 11 on an outer surface, and a proximal end of which extends in an arc shape having the first axis Ax1 as its center is formed. This projection portion 818 has thickness substantially the same as the width of the concave portion 97. In the modification 2-1, three pieces of the projection portions 818 are provided, and are arranged to be rotationally symmetric at 120° about the first axis Ax1. Furthermore, a locus of distal ends of the three projection portions 98 forms a circular shape having a diameter substantially the same as the inner diameter of the bush main body 961. The coupler 9A is attached to the casing 8C as the three projection portions 818 respectively engage with (fit in) the concave portion 97 in a state in which an opening of the bottomed-cylindrical shape is directed to the left side in FIG. 11. In this state, the center axis Ax2 agrees with the first axis Ax1. Moreover, the coupler 9C is restricted its movement to a direction of the first axis Ax1 relative to the casing 8C, and is rotatable relative to the casing 8C about the first axis Ax1 (the center axis Ax2).

The outer surface of the projection portion 818 is a portion that slides on the inner surface of the concave portion 97, and corresponds to the second rotation-sliding surface according to the present invention.

That is, the outer surface of the projection portion 818 (the second rotation-sliding surface according to the present invention) abuts only on a part of the inner surface of the concave portion 97 (the first rotation-sliding surface according to the present invention), in the state in which relative rotation of casing 8C and the coupler 9A about the first axis Ax1 is stopped, to expose a part of the inner surface of the concave portion 97.

As in the modification 2-1 described above, also when the first member according to the present invention is the coupler 9A, and the second member according to the present invention is the casing 8C, a similar effect as the second embodiment described above is produced.

Modification 2-2 of Second Embodiment

Figure 13:
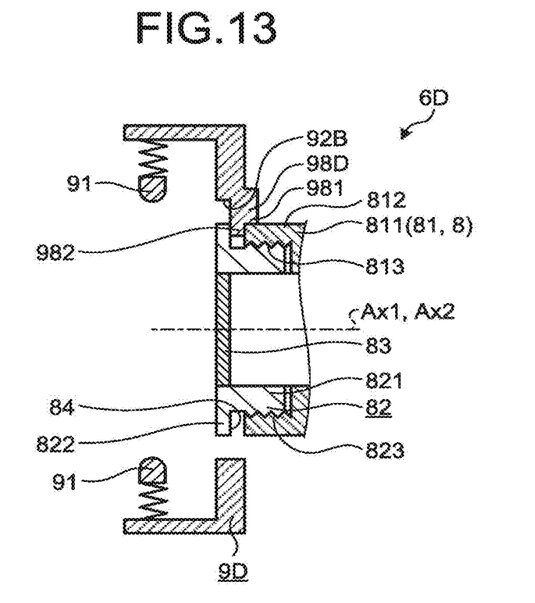
FIG. 13 is a diagram illustrating a modification 2-2 of the second embodiment.

FIG. 13 is a diagram illustrating a modification 2-2 of the second embodiment. Specifically, FIG. 13 is a diagram corresponding to FIG. 7.

In the second embodiment described above, a projection portion 98D may be used instead of the projection portion 98 as in an endoscope camera head 6D (coupler 9D) according to the modification 2-2 illustrated in FIG. 13.

The projection portion 98D includes a projection-portion main body 981 and a convex portion 982 as illustrated in FIG. 13.

The projection-portion main body 981 is a portion that protrudes toward the center axis Ax2 from a right end rim side in FIG. 13 on the inner circumferential surface of the through hole 92B. A proximal end of this projection-portion main body 981 extends in an arc shape having the center axis Ax2 (the first axis Ax1) as its center.

Moreover, the projection-portion main body 981 has thickness larger than the width of the concave portion 84. Furthermore, a locus of distal ends of the three projection portions 981 forms a circular shape having a diameter substantially the same as the outer diameter of the jut-out portion 812

The convex portion 982 protrudes toward the center axis Ax2 from a left end rim side in FIG. 13 at the distal end of the projection-portion main body 981. This convex portion 982 has thickness substantially the same as the width of the concave portion 84. Moreover, a locus of distal ends of the three convex portions 982 forms a circular shape having a diameter smaller than the outer diameter of the jut-out portion 812, and larger than the outer diameter of the bush main body 821.

As described above, the distal end of the projection portion 98D is formed in a stepped-shape along the center axis Ax2 by the convex portion 982.

With the structure described above, the coupler 9D is attached to the casing 8 as the three convex portions 982 respectively engage with (fit in) the concave portion 84 in a state in which an opening of the bottomed-cylindrical shape is directed to a left side in FIG. 13, and as the distal end of the projection-portion main body 981 abuts on the outer circumferential surface of the jut-out portion 812. In this state, the center axis Ax2 agrees with the first axis Ax1. Moreover, the coupler 9D is restricted its movement to the direction of the first axis Ax1 relative to the casing 8, and is rotatable relative to the casing 8 about the first axis Ax1 (the center axis Ax2).

The inner surface of the concave portion 84 and the outer circumferential surface and the jut-out portion 812 are portions on which the coupler 9D slides, and corresponds to the first rotation-sliding surface according to the present invention. Moreover, the outer surface of the projection portion 98D (the distal end of the projection-portion main body 981 and the outer surface of the convex portion 982) is a portion that slides on the inner surface of the concave portion 84 and on the outer circumferential surface of the jut-out portion 812, and corresponds to the second rotation-sliding surface according to the present invention.

That is, the outer surface of the projection portion 98D (the second rotation-sliding surface according to the present invention) abuts only on a part of the inner surface of the concave portion 84 and of the outer circumferential surface of the jut-out portion 812 (the first rotation-sliding surface according to the present invention) in a state in which relative rotation of the casing 8 and the coupler 9D about the first axis Ax1 is stopped, to expose a part of the inner surface of the concave portion 84 and of the outer circumferential surface of the jut-out portion 812 outside.

According to the modification 2-2 described above, in addition to the effect similar to the second embodiment described above, a following effect is produced.

In the endoscope camera head 6D according to the modification 2-2, the outer circumferential surface of the jut-out portion 812 and the distal end of the projection-portion main body 981 form a part of the first and the second rotation-sliding surfaces according to the present invention. That is, not a portion deep inside, but a portion easy to clean forms a part of the first and the second rotation-sliding surfaces according to the present invention. Therefore, cleaning is made further easier, and cleaning time can be further reduced.

Modification 2-3 of Second Embodiment

Figure 14:
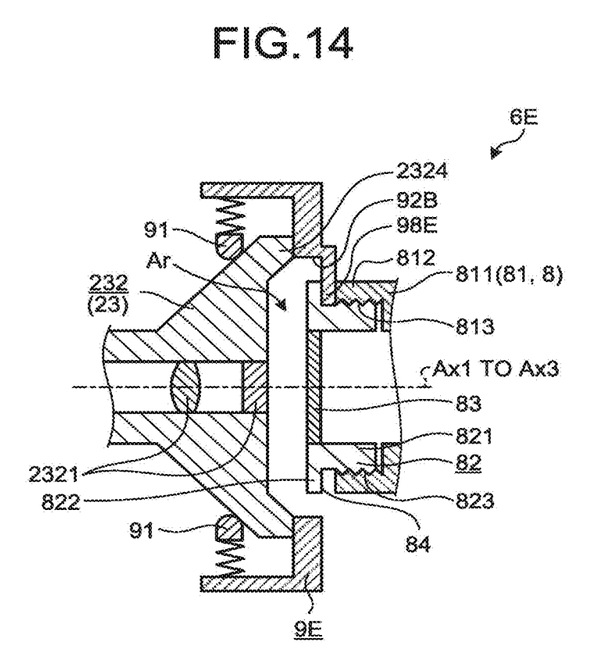
FIG. 14 is a diagram illustrating a modification 2-3 of the second embodiment.

FIG. 14 is a diagram illustrating a modification 2-3 of the second embodiment. Specifically, FIG. 14 is a diagram corresponding to FIG. 7.

In the second embodiment described above, as in an endoscope camera head BE (coupler 9E) according to the modification 2-3 illustrated in FIG. 14, a projection portion 98E may be used instead of the projection portion 98.

The projection portion 98E is arranged at a position offset to right side (side apart from the eyepiece 232) from the projection portion 98 described in the second embodiment.

According to the modification 2-3 described above, in addition to an effect similar to the second embodiment, a following effect is produced.

In the endoscope camera head 6E according to the modification 2-3, the projection portion 98E is arranged at a position offset to a direction apart from the eyepiece 232. That is, by expanding the space Ar, sufficient ventilation is achieved. Therefore, it is possible to suppress formation of condensation on the eyepiece optical system 2321 or the optical device 83 effectively, and to significantly reduce drying time when condensation is formed.

Other Embodiments

Embodiments to implement the present invention have been described, but the present invention is not limited only to the first and the second embodiments and the modifications 1-1, 2-1 to 2-3 described above.

Figure 15:
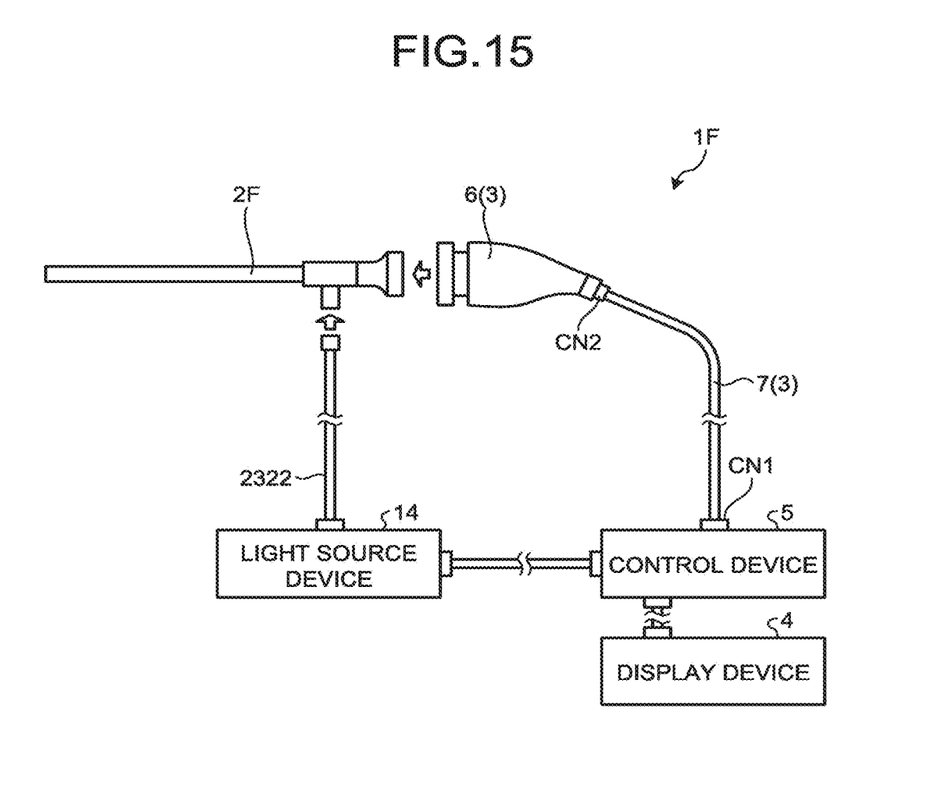
FIG. 15 is a diagram illustrating a modification 3-1 of the first and the second embodiments.

FIG. 15 is a diagram illustrating a modification 3-1 of the first and the second embodiments.

In the first and the second embodiments and the modifications 1-1, 2-1 to 2-3, the endoscope camera heads 6, 6A to 6E are detachably provided with respect to the resectscope 2 for urinary organs, but it is not limited thereto. As in an endoscope device 1F according to the modification 3-1 illustrated in FIG. 15, the endoscope camera head 6 may be detachably provided, for example, with respect to an endoscope 2F for digestive organs.

The endoscope 2F is constituted of a rigid endoscope. That is, the endoscope 2F is hard or at least a part thereof is flexible and has a thin and long shape, to be inserted into a living body. In this endoscope 2F, an optical system that is constituted of one or more lenses, and gathers a subject image is provided. Light supplied from a light source device 14 (FIG. 15) to the light guide 2322 is emitted from a distal end of the endoscope 2F, to be irradiated to an inside of the living body. The light irradiated inside the living body and reflected inside the living body (subject image) is gathered by the optical system in the endoscope 2F. The endoscope camera head 6 images the subject image gathered by the optical system in the endoscope 2F.

Moreover, not limited to a rigid endoscope, the endoscope 2F may be a flexible endoscope.

In the first and the second embodiments, and the modifications 1-1, 2-1 to 2-3, 3-1, the endoscope devices 1, 1F may be an endoscope device that is used in an industrial field, and that observes inside a subject, such as a mechanical structure.

In the first embodiment and the modification 1-1 described above, the grooves according to the present invention (the groove portions 94, 815) are arranged in the convex portions 93, 814, but it is not limited thereto, and may be arranged in the concave portions 84, 97.

In the second embodiment and the modifications 2-1 to 2-3 described above, the number of the projection portions according to the present invention (the projection portions 98, 98D, 98E, 818) is not limited to three, but may be one, two, four, or more.

REFERENCE SIGNS LIST 1, 1F ENDOSCOPE DEVICE
2 RESECTSCOPE
2F ENDOSCOPE
3 ENDOSCOPE IMAGING DEVICE
4 DISPLAY DEVICE
5 CONTROL DEVICE
6, 6A TO 6E ENDOSCOPE CAMERA HEAD
7 CABLE
8, 8A, 8C CASING
9, 9A, 9B, 9D COUPLER
10 PRISM
11 LENS UNIT
12 IMAGING UNIT
13 OPERATING UNIT
14 LIGHT SOURCE DEVICE
21 SHEATH
22 GUIDE TUBE
23 ENDOSCOPE
24 RESECT ELECTRODE MEMBER
25 HANDLE PORTION
81, 81A, 81C CASING MAIN BODY
82 ATTACHMENT BUSH
83 OPTICAL DEVICE
84 CONCAVE PORTION
91 PRESSURIZING PORTION
92, 92B THROUGH HOLE
93 CONVEX PORTION
94 GROOVE PORTION
95 COUPLER MAIN BODY
96 ATTACHMENT BUSH
97 CONCAVE PORTION
98, 98D, 98E PROJECTION PORTION
221 MOUNTING MEMBER
222 WATER SUPPLY INLET
231 INSERTION PORTION
232 EYEPIECE
251 FIXING RING
252 SLIDER
253 SPRING MEMBER
811, 811A, 811C PROTRUSION PORTION
812 JUT-OUT PORTION
813 SCREW GROOVE
814 CONVEX PORTION
815 GROOVE PORTION
816, 817 BOTH END PORTION

818 PROJECTION PORTION
821 BUSH MAIN BODY
822 JUT-OUT PORTION
823 SCREW GROOVE
941, 942 BOTH END PORTION
951 THROUGH HOLE
952 JUT-OUT PORTION
953 SCREW GROOVE
961 BUSH MAIN BODY
962 JUT-OUT PORTION
963 SCREW GROOVE
981 PROJECTION-PORTION MAIN BODY
982 CONVEX PORTION
2321 EYEPIECE OPTICAL SYSTEM
2322 LIGHT GUIDE
2323 LIGHT SOURCE CONNECTOR
2324 EXPANDING PORTION
2521 HIGH-FREQUENCY POWER CORD
2522 POWER SOURCE CONNECTOR
2523 FINGER HOOK MEMBER
Ar SPACE
Ax1 FIRST AXIS
Ax2 CENTER AXIS
Ax3 ENDOSCOPE OPTICAL AXIS
Ax4 IN-CASE OPTICAL AXIS
CN1, CN2 CONNECTOR
O CENTER OF GRAVITY

The invention claimed is:

1. An endoscope camera head comprising
a first member and a second member that are capable of rotating relative to each other about a first axis, wherein
the first member has a concave portion that extends in an annular shape about the first axis as a center is provided, and a first rotation-sliding surface that extends in an annular shape about the first axis as a center, wherein the first rotation-sliding surface includes an inner surface of the concave portion,
the second member is configured to engage with the first rotation-sliding surface and has a convex portion that extends in an annular shape about the first axis as a center and engages with the concave portion, and a second-rotation sliding surface configured to rotation-slide relatively to the first rotation-sliding surface, wherein the second rotation-sliding surface includes an outer surface of the convex portion, and
at a distal end of the convex portion, a groove that extends in a spiral shape, so that the second rotation-sliding surface abuts only on a part of the first rotation-sliding surface, to expose a part of the first rotation-sliding surface outside.

2. The endoscope camera head according to claim 1, wherein
respective parts of both end portions of the groove in a direction of the first axis are positioned outside the concave portion.

3. The endoscope camera head according to claim 1, comprising:
a coupler holding an endoscope configured to capture and output a subject image; and
a camera-head that includes a casing supporting the coupler rotatably about the first axis, and an image sensor housed in the casing, the image sensor being configured to image the subject image emitted from the endoscope, wherein
the first member is the casing, and
the second member is the coupler.

4. The endoscope camera head according to claim 1, comprising:
a coupler holding an endoscope configured to capture and output a subject image; and
a camera-head that includes a casing supporting the coupler rotatably about the first axis, and an image sensor housed in the casing, the image sensor being configured to image the subject image emitted from the endoscope, wherein
the first member is the coupler, and
the second member is the casing.

5. The endoscope camera head according to claim 1, wherein the second member is configured to engage with the first rotation-sliding surface in a state in which movement to a direction of the first axis is restricted relative to the first member.

6. The endoscope camera head according to claim 1, wherein the second member includes a protrusion that extends along a direction of the first axis.

7. The endoscope camera head according to claim 6, wherein the protrusion is a cylinder.

8. The endoscope camera head according to claim 1, wherein the first member includes a main body that extends from the concave portion along a direction of the first axis.

9. The endoscope camera head according to claim 8, wherein the main body is a cylinder.

10. The endoscope camera head according to claim 8, wherein the main body includes a screw groove on an outer surface thereof.

* * * * *